(12) United States Patent
Kinlaw, III

(10) Patent No.: US 7,906,294 B2
(45) Date of Patent: Mar. 15, 2011

(54) PROGNOSIS AND TREATMENT OF BREAST CANCER

(75) Inventor: William B. Kinlaw, III, Etna, NH (US)

(73) Assignee: Trustees of Dartmouth College, Hanover, NH (US)

( * ) Notice: Subject to any disclaimer, the term of this patent is extended or adjusted under 35 U.S.C. 154(b) by 401 days.

(21) Appl. No.: 11/912,413

(22) PCT Filed: May 12, 2006

(86) PCT No.: PCT/US2006/018527
§ 371 (c)(1),
(2), (4) Date: Oct. 24, 2007

(87) PCT Pub. No.: WO2006/124661
PCT Pub. Date: Nov. 23, 2006

(65) Prior Publication Data
US 2009/0232818 A1    Sep. 17, 2009

Related U.S. Application Data

(60) Provisional application No. 60/737,223, filed on Nov. 16, 2005, provisional application No. 60/681,683, filed on May 17, 2005.

(51) Int. Cl.
*C12Q 1/00* (2006.01)
*G01N 1/00* (2006.01)
*G01N 33/48* (2006.01)
*G01N 33/53* (2006.01)
*G01N 33/567* (2006.01)
*G01N 33/574* (2006.01)

(52) U.S. Cl. ............ 435/7.23; 435/4; 435/7.1; 435/7.21; 436/63; 436/64; 436/174

(58) Field of Classification Search .................. None
See application file for complete search history.

(56) References Cited

U.S. PATENT DOCUMENTS
2005/0112118 A1    5/2005    Cimbora et al.

OTHER PUBLICATIONS

Cunningham et al. "Spot 14" protein: a metabolic integrator in normal and neoplastic cells. Thyroid 8(9): 815-825, Sep. 1998.*
Campbell et al., "Human Spot 14 Glucose and Thyroid Hormone Response: Characterization and Thyroid Hormone Response Element Identification", Endocrinology 2003 144(12):5242-5248.
Cunningham et al., ""Spot 14" protein: a metabolic integrator in normal and neoplastic cells", Thyroid 1998 8(9):815-825, Abstract only.
Heemers et al., "Progestins and Androgens Increase Expression of Spot 14 in T47-D Breast Tumor Cells", Biochemical and Biophysical Research Communications 2000 269:209-212.
Joyeux et al., "Progestin Increases Gene Transcription and Messenger Ribonucleic Acid Stability of Fatty Acid Synthetase in Breast Cancer", Molecular Endocrinology 1989 4:681-686.
Kinlaw et al., "Minireview: Spot 14: A Marker of Aggressive Breast Cancer and Potential Therapeutic Target", Endocrinology 2006 147:4048-4055.
Lieberman et al., "The Constitution of a Progesterone Response Element", Molecular Endocrinology 1993 7:515-527.
Moncur et al., "The "Spot 14" gene resides on the telomeric end of the 11q13 amplicon and is expressed in lipogenic breast cancers: Implications for control of tumor metabolism", Proc. Natl. Acad. Sci. USA 1998 95:6989-6994.
Sanchez-Rodriguez et al., "The spot 14 protein inhibits growth and induces differentiation and cell death of human MCF-7 breast cancer cells", Biochem. J. 2005 390:57-65.
Wells et al., "Expression of "Spot 14" (THRSP) predicts disease free survival in invasive breast cancer: immunohistochemical analysis of a new molecular marker", Breast Cancer Research and Treatment 2006 98:231-240.

* cited by examiner

*Primary Examiner* — Alana M Harris
(74) *Attorney, Agent, or Firm* — Licata & Tyrrell P.C.

(57) ABSTRACT

The present invention relates to an antibody which specifically binds a Spot 14 (S14 or THRSP) protein in human breast cancer cells and a method for using the same to predict disease-free survival and select treatment modalities for breast cancer. The present invention is also a method for inducing apoptosis in breast cancer cells by inhibiting the expression or activity of Spot 14. Compositions and methods for treating breast cancer are also provided.

1 Claim, 1 Drawing Sheet

SEQUENCE LISTING

```
<160> NUMBER OF SEQ ID NOS: 23

<210> SEQ ID NO 1
<211> LENGTH: 146
<212> TYPE: PRT
<213> ORGANISM: Homo sapiens

<400> SEQUENCE: 1

Met Gln Val Leu Thr Lys Arg Tyr Pro Lys Asn Cys Leu Leu Thr Val
1               5                   10                  15

Met Asp Arg Tyr Ala Ala Glu Val His Asn Met Glu Gln Val Val Met
            20                  25                  30

Ile Pro Ser Leu Leu Arg Asp Val Gln Leu Ser Gly Pro Gly Gly Gln
        35                  40                  45

Ala Gln Ala Glu Ala Pro Asp Leu Tyr Tyr Phe Thr Met Leu Lys
    50                  55                  60
```

```
Ala Ile Cys Val Asp Val Asp His Gly Leu Leu Pro Arg Glu Glu Trp
 65                  70                  75                  80

Gln Ala Lys Val Ala Gly Ser Glu Glu Asn Gly Thr Ala Glu Thr Glu
                 85                  90                  95

Glu Val Glu Asp Glu Ser Ala Ser Gly Glu Leu Asp Leu Glu Ala Gln
            100                 105                 110

Phe His Leu His Phe Ser Ser Leu His His Ile Leu Met His Leu Thr
        115                 120                 125

Glu Lys Ala Gln Glu Val Thr Arg Lys Tyr Gln Glu Met Thr Gly Gln
    130                 135                 140

Val Trp
145

<210> SEQ ID NO 2
<211> LENGTH: 20
<212> TYPE: DNA
<213> ORGANISM: Artificial sequence
<220> FEATURE:
<223> OTHER INFORMATION: Synthetic siRNA

<400> SEQUENCE: 2
tacgtcggca atgctgacat                                                 20

<210> SEQ ID NO 3
<211> LENGTH: 20
<212> TYPE: DNA
<213> ORGANISM: Artificial sequence
<220> FEATURE:
<223> OTHER INFORMATION: Synthetic siRNA

<400> SEQUENCE: 3
tatgttggca atgctgacat                                                 20

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
ggaaatgacg ggacaagtt                                                  19

<210> SEQ ID NO 5
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 5
cagccgaggt gcacaacat                                                  19

<210> SEQ ID NO 6
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 6
ggatggcaag catgtggtg                                                  19
```

```
<210> SEQ ID NO 7
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 7
tgtccacagt cagcaatgg                                                   19

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
ccatctgtgt ggatgtggac c                                                21

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
agcatcccgg agaactgagc c                                                21

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 10
tcagcgaggc ggctttggag cag                                              23

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
catgtcttcg atgtcggtca g                                                21

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
ggaggggtag ggccaacggc ct                                               22

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 13
```
catgtcttcg aaagtgcaat cc                                          22

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 14
acagggacaa cctggagttc t                                           21

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
ctgtggtccc acttgatgag t                                           21

<210> SEQ ID NO 16
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 16
acccggccga ccatccc                                                17

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
agtttgcagt ctgcccttcc c                                           21

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ccgggttaga caacgatgtt                                             20

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
tggctgtaca tgtcccgaga g                                           21

<210> SEQ ID NO 20
<211> LENGTH: 21
<212> TYPE: DNA
<213> ORGANISM: Artificial sequence

```
<220> FEATURE:
<223> OTHER INFORMATION: Synthetic oligonucleotide

<400> SEQUENCE: 20
acctcacctc ggcacagtgc t                                              21

<210> SEQ ID NO 21
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 21
tcacccggct ccttgtcct                                                 19

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
ccgcctgagg atgcctacgt c                                              21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
ggaggcggga gttggtaaag a                                              21
```

PROGNOSIS AND TREATMENT OF BREAST CANCER

This application claims benefit of U.S. Provisional Patent Application Ser. Nos. 60/737,223, filed Nov. 16, 2005, and 60/681,683, filed May 17, 2005, the contents of which are incorporated herein by reference in their entireties.

This invention was made in the course of research sponsored by the National Institutes of Health (Grant No. RO1 DK58961-01A2). The U.S. government may have certain rights in this invention.

BACKGROUND OF THE INVENTION

Spot 14, also known as thyroid hormone-responsive Spot 14 (THRSP) or S14, is a primarily nuclear protein that is abundant in tissues active in long chain fatty acid synthesis, including lactating mammary gland (Cunningham, et al. (1998) *Thyroid* 8:815-825). It has been shown that the S14 gene is located on chromosome 11q13 and is overexpressed in most breast cancers (Moncur, et al. (1998) *Proc. Natl. Acad. Sci. USA* 95:6989-6994). Concordant overexpression of S14 and acetyl CoA-carboxylase, the rate-determining enzyme of long-chain fatty acid synthesis, indicates that S14 is a component of the lipogenic phenotype observed in aggressive breast cancers.

The lipogenic tumor phenotype is characterized by high rates of fatty acid synthesis, elevated tumor content of lipogenic enzymes such as fatty acid synthase (FAS), and dependence on lipogenesis for tumor cell growth (Kuhajda (2000) *Nutrition* 16:202-2). Cerulenin, a pharmacological inhibitor of fatty acid synthase has been shown to cause apoptosis of breast cancer cells (Pizer, et al. (1996) *Cancer Res.* 56:2745-2747), and inhibit the growth of human ovarian tumor cell xenografts in nude mice (Pizer, et al. (1996) *Cancer Res.* 56:1189-1193). Likewise, the anti-obesity drug Orlistat, also a FAS inhibitor, causes apoptosis of lipogenic prostate cancer cells in culture and in xenografts in immunodeficient mice (Kridel, et al. (2004) *Cancer Res.* 64:2070-2075).

In hepatocytes, S14 and lipogenic enzymes are inducible by insulin, glucose metabolism, and thyroid hormone (Cunningham, et al. (1998) supra). The lipogenic effects of insulin are substantially mediated at the gene level by sterol response element-binding protein 1c (SREBP-1c), a transcription factor that resides in the endoplasmic reticulum until insulin activates its translocation to the Golgi, where the active fragment is released by proteolysis, permitting transit to the nucleus to activate gene transcription (Foretz, et al. (1999) *Proc. Natl. Acad. Sci. USA* 96:12737-12742; Rawson (2003) *Nat. Rev. Mol. Cell. Biol.* 4:631-640). As in the liver, SREBP-1c may be the major driver of lipogenic gene expression. This issue has been addressed in studies of breast cancer specimens (Yang, et al. (2003) *Exp. Cell Res.* 282:132-137), colon cancer specimens and cells (Li, et al. (2000) *Exp. Cell. Res.* 261:159-165), and prostate cancer cells (Swinnen, et al. (1997) *Proc. Natl. Acad. Sci. USA* 94:12975-12980; Swinnen, et al. (2000) *Oncogene* 19:5173-5181; Heemers, et al. (2001) *Mol. Endocrinol.* 15:1817-1828). The studies of breast and colon cancer correlated expression of FAS and SREBP-1c, but did not include mechanistic experiments. Studies in prostate cancer cells, however, directly demonstrated dependence of androgen- and growth factor-induced expression of FAS on SREBP-1c. Moreover, processing of the extranuclear SREBP-1c precursor was increased by androgen induction of SREBP cleavage-activating protein (SCAP), the protein responsible for escorting SREBP-1c to the Golgi, where proteolytic activation occurs. In contrast to the enhancement of SREBP-1c processing by androgen in prostate cancer cells, however, no increase was observed in nuclear SREBP-1c content in progestin-treated T47D cells demonstrating S14 gene induction (Heemers, et al. (2000) *Biochem. Biophys. Res. Comm.* 269:209-212).

A number of other proteins have been identified which may accelerate the growth of breast cancer cells. Such proteins include p53, a transcriptional regulator with tumor suppressor properties, nm23, a putative metastasis suppressor, and several families of cell surface growth factor receptors and their cognate ligands, including the epidermal growth factor (EGF) receptor superfamily, the insulin-like growth factor (IGF-1) family, and the fibroblast growth factor (FGF) family. For example, HER2, a receptor with close similarity to EGF-Receptor, also known as c-erBb-2 (Coussens, et al. (1985) *Science* 230:1132-1139; Yamamoto, et al. (1986) *Nature* 319:230-234; King, et al. (1985) *Nature* 307:521-527) has been identified. This receptor was also isolated as the rat oncogene neu, an oncogene responsible for chemically-induced rat glioblastomas (Padhy, et al. (1982) *Cell* 28:865-871; Schechter, et al. (1984) *Nature* 312:513-516; Bargmann, et al. (1986) *Nature* 319:226-230). HER2/erbB-2 is known to be amplified and overexpressed in about 25% of human breast cancers (Slamon, et al. (1987) *Science* 235:177-182; Slamon, et al. (1989) *Science* 244:707-712).

SUMMARY OF THE INVENTION

The present invention is a method of predicting disease-free survival of a subject with breast cancer. The method involves detecting the expression level of S14 in a sample obtained from a subject with breast cancer, comparing the level in the sample with a control, wherein a lack of overexpression of S14 in the sample compared to the control is predictive of prolonged disease-free survival.

The present invention is also a method for selecting a therapeutic modality for the treatment of breast cancer. The method involves detecting the expression level of S14 in a sample obtained from a subject with breast cancer, comparing the level in the sample with a control, and selecting a therapeutic modality based upon the expression level of S14 in the sample.

The present invention is further an isolated antibody, antibody fragment, or antibody derivative which is selected for specifically binding to an S14 protein of SEQ ID NO:1 in breast tissue or cells. An isolated hybridoma for producing the antibody and a kit containing the antibody, antibody fragment, or antibody derivative are also provided.

A method for inducing apoptosis in a breast cancer cell is also provided. This method involves contacting a breast cancer cell with an agent that inhibits the expression or activity of Spot 14 thereby inducing apoptosis.

The present invention is also a method for treating breast cancer by administering to a subject with breast cancer an effective amount of an agent that inhibits the expression or activity of Spot 14 so that apoptosis in breast cancer cells in the subject is induced and the breast cancer is treated.

A composition composed of an agent that inhibits the expression or activity of Spot 14 and a pharmaceutically acceptable carrier for the treatment of breast cancer is also provided.

The present invention is further a method for identifying an agent that induces apoptosis in a breast cancer cell. The method involves the steps of contacting a breast cancer cell with a test agent and determining the expression or activity of Spot 14 in the breast cancer cell, wherein a decrease in the expression or activity of Spot 14 in the breast cancer cell contacted with the test agent, compared to a breast cancer cell not contacted with the test agent, is indicative of an agent that induces apoptosis in a breast cancer cell.

The present invention is also a method for identifying an agent that induces apoptosis in a breast cancer cell by contacting Spot 14 with a test agent and determining the multimerization of Spot 14, wherein a decrease in the multimerization of Spot 14 contacted with the test agent, compared to multimerization of Spot 14 not contacted with the test agent, is indicative of an agent that induces apoptosis in a breast cancer cell. Agents identified by the screening methods of the invention are also provided.

BRIEF DESCRIPTION OF THE DRAWINGS

FIG. 1A, analysis of S14 staining in DCIS (n=44) as a function of histological grade. FIG. 1B, pooled data from invasive breast cancers without (n=34) or with (n=54) lymph node metastases at the time of diagnosis, stratified by tumor grade. FIG. 1C, pooled data from invasive cases (n=88) as a function of tumor size.

DETAILED DESCRIPTION OF THE INVENTION

Figure 1:
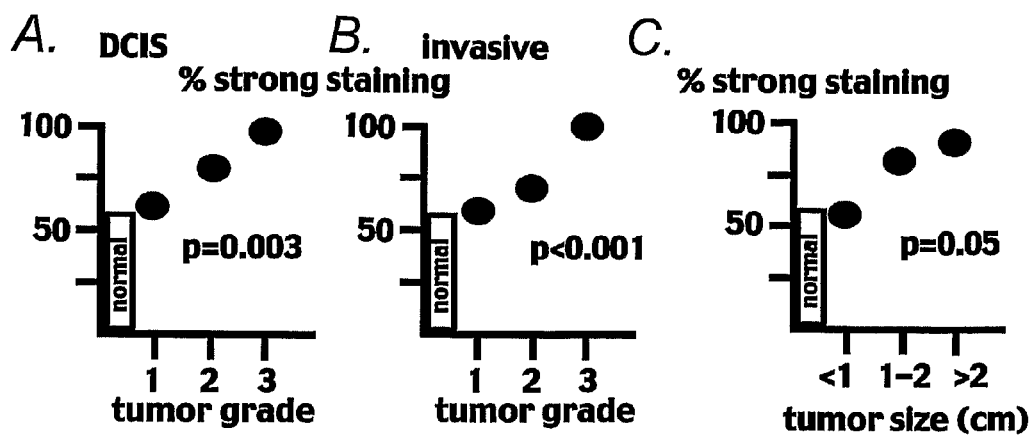
FIG. 1 shows the relationship of S14 content to tumor grade and size. The frequency of strong staining in normal mammary tissue is indicated by the bar on the y-axis.

It has now been found that S14 is a marker for aggressive breast cancers. Moreover, S14 expression has been demonstrated as being required for the growth and survival of breast cancer cells, as inhibiting the expression of S14 was found to induce apoptosis. Accordingly, in addition to being useful as a prognostic marker, S14 is also useful as a target for therapeutic agents in the treatment of breast cancer.

Increased levels of S14 expression in tumors strongly correlated with tumor aggressiveness. The frequency of maximal S14 expression exhibited a strong positive correlation with tumor grade in both in situ and invasive cases, and was also associated with larger tumor size. Further, S14 overexpression was not acquired during tumor progression and the S14 score did not co-segregate with that of the conventional tumor markers (sex steroid receptors, Her2/neu) or cyclin D1. Accordingly, the present invention relates to the use of S14 as a marker for predicting or prognosticating disease-free survival of a subject with breast cancer, or alternatively predicting cancer-attributable death, including recurrence, of breast cancer in a subject. By detecting the level of expression of S14 in a sample from the subject and comparing the expression of S14 in the sample with the expression of S14 in a control, it can be predicted whether the subject has a non-aggressive form of cancer and therefore, with treatment, an increase in the number of years of disease-free survival.

In carrying out the methods of the present invention, the level of expression of S14 protein in a sample can be detected using any one of a variety of immunoassay methods with qualitative or quantitative results. For a review of immunological and immunoassay procedures in general, see Stites and Terr, ed. (1991) Basic and Clinical Immunology 7th Edition. Moreover, the immunoassays of the present invention can be performed in any of several configurations, which are reviewed extensively in Enzyme Immunoassay ((1980) Maggio, ed., CRC Press, Boca Raton, Fla.) and Practice and Theory of Enzyme Immunoassays ((1985) Tijssen, ed., Elsevier, Amsterdam, The Netherlands). It is contemplated that either an absolute, semi-quantitative, or relative level of S14 expression can be detected using the immunoassays disclosed herein.

While the level of S14 expression can be detected by analyzing said levels in breast tissue samples or aspirated breast cell samples (e.g., a biopsy sample or is situ imaging), it is contemplated that the level of S14 could also be detected in a bodily fluid (e.g., a blood sample or a sample of fluid obtained by breast duct lavage). In general, the sample can be obtained from a subject diagnosed with breast cancer or a subject suspected of being at risk of having breast cancer (e.g., because of environmental factors or family history). For these subjects the method of the invention is useful for selecting a suitable therapeutic course of treatment. Alternatively, the sample can be obtained from a subject that has been treated for breast cancer, wherein prognosis is desired to determine whether the subject has an aggressive form of cancer which will recur and require more aggressive initial therapy and closer monitoring and follow-up.

In one embodiment, an immunoassay to detect or measure S14 levels in a human sample uses an isolated antibody (e.g., polyclonal or monoclonal), antibody fragment, or antibody derivative which was raised to an isolated S14 protein of SEQ ID NO:1 or a fragment thereof and selected for specifically binding to an S14 protein in breast tissue or cells. The antibody, antibody fragment, or antibody derivative is further selected to have low cross-reactivity against non-target proteins and any such cross-reactivity is removed by immunoabsorption prior to use in the immunoassay.

As used herein, an antibody refers to a polypeptide substantially encoded by an immunoglobulin gene or immunoglobulin genes, or fragments thereof which specifically bind and recognize an antigen. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit includes a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. In one embodiment, the antibody of the instant invention is polyclonal. In another embodiment, the antibody of the instant invention is monoclonal.

For the production of polyclonal or monoclonal antibodies, either recombinant S14 protein or naturally occurring S14 protein (e.g., in pure or impure form) can be used as antigen or immunogen. In particular embodiments, synthetic peptides of immunogenic portions of the S14 protein (e.g., SEQ ID NO:1) are used as an antigen for the production of antibodies to the S14 protein. Immunogenic portions of S14 can be readily identified by the skilled artisan using any art-established computer algorithm for identifying such antigenic sequences (see, e.g., Jamison and Wolf (1988) *Bioinformatics* 4:181-186; Carmenes, et al. (1989) *Biochem Biophys Res Commun.* 159(2):687-93).

For the production of polyclonal antibodies, various host animals can be immunized by injection with the S14 antigen including but not limited to rabbits, mice, rats, etc. Various adjuvants can be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (Bacille Calmette-Guerin) and *Corynebacterium parvum*.

A monoclonal antibody, which is a substantially homogeneous population of antibodies to a particular antigen, can be obtained by any technique which provides for the production of antibody molecules by continuous cell lines in culture. These include, but are not limited to the hybridoma technique of Kohler and Milstein ((1975) *Nature* 256:495-497) and U.S. Pat. No. 4,376,110; the human B-cell hybridoma technique (Kosbor, et al. (1983) *Immunology Today* 4:72; Cole, et al. (1983) *Proc. Natl. Acad. Sci. USA* 80:2026-2030); and the EBV-hybridoma technique (Cole, et al. (1985) Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the monoclonal antibody of this invention can be cultivated in vitro or in vivo. Desirably, monoclonal antibodies are produced in vivo because of the high titers obtained.

Chimeric antibodies are also contemplated. Techniques developed for the production of chimeric antibodies (Morrison, et al. (1984) *Proc. Natl. Acad. Sci. USA* 81:6851-6855; Neuberger, et al. (1984) *Nature* 312:604-608; Takeda, et al. (1985) *Nature* 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region.

Antibodies can also be modified, e.g., to produce a number of well-characterized fragments generated by digestion with various peptidases. For example, pepsin digestion of an antibody produces F(ab')$_2$. The F(ab')$_2$ can further be reduced under mild conditions to break the disulfide linkage in the hinge region, thereby converting the F(ab')$_2$ dimer into an Fab' monomer. The Fab' monomer is essentially a Fab with part of the hinge region (see, Fundamental Immunology, Third Edition (1993) W. E. Paul, ed., Raven Press, NY). While various antibody fragments are defined in terms of the digestion of an intact antibody, one of skill will appreciate that such fragments can be synthesized de novo either chemically or by utilizing recombinant DNA methodology. Accordingly, the term antibody fragment also includes fragments either produced by the modification of whole antibodies or those synthesized de novo using recombinant DNA methodologies. Thus, an antibody fragment includes, but is not limited to, single chain antibodies, Fab fragments, F(ab')$_2$ fragments, diabodies (Holliger, et al. (1993) *Proc. Natl. Acad. Sci. USA* 90:6444; Poljak (1994) *Structure* 2:1121-1123), fragments produced by a Fab expression library (Huse, et al. (1989) *Science* 246:1275-1281), and epitope-binding fragments of any of the above.

Antibody derivatives such as peptide aptamers, which are selected for specifically binding to an S14 protein in breast tissue or cells, are also provided in the instant invention. Peptide aptamers can be rationally designed or screened for in a library of aptamers (e.g., provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range).

The phrase "specifically (or selectively) binding to an S14 protein in breast tissue or cells" refers to a binding reaction which is determinative of the presence of the S14 protein in its native, three-dimensional conformation in the presence of a heterogeneous population of proteins and other biologics. Thus, under designated immunoassay conditions, the specified antibodies bind to S14 protein and do not bind in a significant amount to other proteins present in the sample. Specific binding of an antibody under such conditions may require an antibody that is selected for its specificity for S14 protein. For example, antibodies raised to an S14 protein fragment of SEQ ID NO:1 can be selected to obtain antibodies specifically immunoreactive with S14 protein in its native conformation in breast tissue or breast cells and not with other proteins except for polymorphic variants. Typically a specific or selective reaction will be at least twice background signal or noise and more typically more than 10 to 100 times background. A variety of immunoassay formats can be used to select antibodies specifically immunoreactive with S14 in breast tissue or breast cells. For example, solid-phase ELISA immunoassays, western blot analysis, or immunohistochemistry are routinely used to select monoclonal antibodies specifically immunoreactive with a protein in a particular tissue or cell. See Harlow and Lane (1988) Antibodies, A Laboratory Manual, Cold Spring Harbor Publications, New York, for a description of immunoassay formats and conditions that can be used to determine specific immunoreactivity. Specific monoclonal and polyclonal antibodies will usually bind with a $K_D$ of at least about 0.1 mM, more usually at least about 1 µM, or at least about 0.1 µM or better.

In particular embodiments, an isolated antibody, antibody fragment, or antibody derivative which is selected for specifically binding to an S14 protein of SEQ ID NO:1 in breast tissue or cells is a component of a kit for detecting the expression level of S14 in a sample. A kit of the invention generally includes a container containing the isolated antibody, antibody fragment, or antibody derivative. The kit can also contain other solutions necessary or convenient for detecting the invention the expression level of S14. The container can be made of glass, plastic or foil and can be a vial, bottle, pouch, tube, bag, etc. The kit may also contain written information, such as procedures for carrying out the method of the present invention or analytical information, such as the amount of reagent contained in the first container means and representative images of breast cancer tumor samples with no detectable S14 expression (e.g., semi-quantitatively graded 0), low level S14 expression (e.g., semi-quantitatively graded +1) or a high level of S14 expression (e.g., semi-quantitatively graded +2). The container can be in another container, e.g., a box or a bag, along with the written information.

As indicated supra, any one of a variety of immunoassay methods can be used to detect and measure the level of expression of S14 protein in a sample. Typically, such immunoassays often utilize a labeling agent to specifically bind to and label the binding complex formed by the antibody and the antigen. The labeling agent can itself be one of the components of the antibody/antigen complex. Thus, the labeling agent can be a labeled S14 protein or a labeled anti-S14 protein antibody. Alternatively, the labeling agent can be a third moiety, such as another antibody (i.e., a secondary antibody), that specifically binds to the antibody/S14 protein complex. Alternatively, the secondary antibody may lack a label and be bound by a labeled tertiary antibody specific to antibodies of the species from which the secondary antibody is derived. The secondary antibody can be modified with a detectable moiety, such as biotin, to which a third labeled molecule can specifically bind, such as enzyme-labeled streptavidin.

The particular labeling agent or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, TEXAS RED™, rhodamine, and the like), radiolabels (e.g., $^{3}H$, $^{135}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label can be coupled directly or indirectly to the desired component of the assay according to methods well-known in the art. As indicated above, a wide variety of labels can be used, with the choice of label depending on sensitivity required, ease of conjugation with the assay component or moiety, stability requirements, available instrumentation, and disposal provisions.

Non-radioactive labels are often attached by indirect means. Generally, a ligand molecule (e.g., biotin) is covalently bound to the assay component or moiety of interest. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Thyroxine, and cortisol can be used in conjunction with the labeled, naturally occurring anti-ligands. Alternatively, any haptenic or antigenic compound can be used in combination with an antibody.

The components of the assay can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbellif- erone, etc. Chemiluminescent compounds include luciferin, and 2,3-dihydrophthalazinediones, e.g., luminol. For a review of various labeling or signal producing systems which may be used, see, U.S. Pat. No. 4,391,904).

Other proteins capable of specifically binding immunoglobulin constant regions, such as protein A or protein G can also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.* 111:1401-1406 and Akerstrom, et al. (1985) *J. Immunol.* 135:2589-2542).

Immunoassays for detecting S14 protein in samples can be either competitive or noncompetitive. Noncompetitive immunoassays are assays in which the amount of S14 protein is directly measured. In one type of sandwich assay, for example, the anti-S14 protein antibodies can be bound directly to a solid substrate where they are immobilized. These immobilized antibodies then capture S14 protein present in the test sample. S14 protein thus immobilized is then bound by a labeling agent, such as a second S14 protein antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

In competitive assays, the amount of S14 protein present in the sample is measured indirectly by measuring the amount of an added (exogenous) S14 protein displaced (or competed away) from an anti-S14 protein antibody by the S14 protein present in the sample. In one competitive assay, a known amount of, in this case, the S14 protein is added to the sample and the sample is then contacted with an anti-S14 antibody. The amount of S14 protein bound to the antibody is inversely proportional to the concentration of S14 protein present in the sample. In one embodiment, the antibody is immobilized on a solid substrate. The amount of the S14 protein bound to the antibody can be determined either by measuring the amount of S14 protein present in a S14 protein/antibody complex, or alternatively by measuring the amount of remaining uncomplexed protein.

A hapten inhibition assay is another competitive assay. In this assay S14 protein is immobilized on a solid substrate. A known amount of anti-S14 protein antibody is added to the sample, and the sample is then contacted with the immobilized S14 protein. In this case, the amount of anti-S14 protein antibody bound to the immobilized S14 protein is inversely proportional to the amount of S14 protein present in the sample. Again, the amount of immobilized antibody can be detected by detecting either the immobilized fraction of antibody or the fraction of the antibody that remains in solution. Detection can be direct where the antibody is labeled or indirect by the subsequent addition of a labeled moiety that specifically binds to the antibody.

As an alternative to competitive and noncompetitive assays, western blot (immunoblot) analysis can be used to detect and quantify the presence of S14 protein in the sample. The technique generally encompasses separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind S14 protein. These antibodies can be directly labeled or alternatively can be subsequently detected using labeled antibodies (e.g., labeled sheep anti-mouse antibodies) that specifically bind to the anti-S14 protein antibodies.

Immunohistochemical analysis can also be conducted to semi-quantitatively detect the levels of S14 in a tissue sample compared to a control. In general, tissue section samples are overlaid with a blocking solution and subsequently contacted with an anti-S14 antibody. The sample sections are generally overlaid with the antibody solution for 10-20 hours and subsequently washed to remove unbound antibody. The S14 protein/antibody complex is then detected either directly or indirectly as described above. Immunohistochemical techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895-904).

Throughout the assays disclosed herein, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Means of detecting labels are well-known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means a microscope or by photographic film, by the use of electronic detectors such as charge coupled devices (CCDs) or photomultipliers and the like. Similarly, enzymatic labels can be detected by providing the appropriate substrates for the enzyme and detecting the resulting reaction product. Further, simple calorimetric labels can be detected simply by observing the color associated with the label. Thus, in various dipstick assays, conjugated gold often appears pink, while various conjugated beads appear the color of the bead.

While detecting or measuring the level of S14 protein levels are exemplified herein, it is contemplated that the level of S14 mRNA expression could also be used as an indicator of disease-free survival. Methods for detecting the transcript levels are well-known in the art and include, but are not limited to, RT-PCR, chip-based analysis, northern blot analysis, and the like. However, the detection of S14 mRNA in breast cancer samples is desirably carried with samples which have been dissected (e.g., by laser-assisted microdissection) to remove tissues of adipose origin.

Upon cluster analysis, with JAVA TREEVIEW software, of unfiltered data obtained from a 24,000-gene array of 147 cases of breast cancer (University of North Carolina Microarray Database), S14 expression was found to cluster with a group of 29 genes, including several that were readily identifiable as adipocyte-specific, including perilipin, hormone-sensitive lipase, adipocyte fatty acid binding protein 4, adiponectin, and lipoprotein lipase (LPL). This data indicated that the probe used on the arrays contained mRNA from adipocytes of the mammary fat pad. The "co-regulation" of some genes in this cluster may therefore reflect the variable admixture of adipocyte and tumor mRNA.

To examine this further, a panel of cell lines were assessed for expression of LPL mRNA by RT-PCR. Human pre-adipocyte and adipocyte mRNA served as negative and positive controls, respectively. No expression of LPL mRNA was observed in a variety of lipogenic breast cancer cell lines (ZR75.1, SKBR3, MCF7, T47D+/−progestin), or mammary epithelium (MCF10a). Hepatoma (HepG2) and embryonic kidney (HEK293) likewise did not express it. Importantly, a cervical carcinoma line (HeLa) that expresses negligible levels of FAS (Oskouian (2000) *Cancer Letters* 149:43-51), did express LPL mRNA. This indicates that expression of LPL may confer an advantage to tumor cells that have a low capacity for de novo lipogenesis. Overall, these observations confirmed the LPL mRNA detected on breast cancer microarrays was of adipose origin, and indicate that microarray data for genes that are expressed in both breast tumors and adipocytes, such as S14, FAS, and PPAR-γ, are not interpretable unless tumor samples are dissected to obtain probes representative of tumor tissue.

Once the level of S14 expression (protein or mRNA) in the sample is detected or measured, it is compared to the levels of S14 expression in one or more controls in order to predict whether the subject from which the sample was obtained has an aggressive form of cancer and therefore a decrease in the number of years of disease-free survival or whether the subject has a less aggressive form of cancer with a decreased risk of recurrence and increased long-term survival. As exemplified herein, a control can be a sample obtained from healthy subject (i.e., a subject without any signs or symptoms of breast cancer) or can be a representative breast cancer tumor sample with no detectable S14 expression (e.g., semi-quantitatively graded 0), low level S14 expression (e.g., semi-quantitatively graded +1) or a high level of S14 expression (e.g., semi-quantitatively graded +2). By using one or more control samples (e.g., in a panel), the skilled pathologist can compare the intensity of staining of S14 in an immunohistochemical assay for a semi-quantitative, or absolute level of expression of S14 in an ELISA or RT-PCR for a quantitative determination of S14 levels in a test sample from a subject. As exemplified herein, a sample is said to lack S14 overexpression when S14 levels in the sample are comparable to S14 levels in samples from healthy subjects or breast cancer samples graded 0 or +1. In contrast, a sample is said to overexpress S14 when S14 levels in the sample are comparable to S14 levels in breast cancer samples graded +2. In accordance with the method of the invention, subjects lacking S14 overexpression will generally survive, following surgical removal or the primary tumor and/or chemotherapy, for a certain period of time without cancer recurrence (i.e., prolonged disease-free survival), whereas subjects with S14 overexpression generally have a more aggressive form of cancer and therefore an increased risk of cancer recurrence with treatment. As used herein, prolonged disease-free survival is intended to mean disease-free survival (i.e., no breast cancer recurrence) for generally more than 5 years after treatment, or more specifically more than 8 years after treatment, or more desirably at least 10 years after treatment.

The predictive method of the present invention can be used clinically to make treatment decisions by choosing the most appropriate treatment modalities for any particular subject. The predictive methods of the present invention are valuable tools in predicting if a subject is likely to respond favorably to a treatment regimen, such as surgical intervention, chemotherapy with a given drug or drug combination, and/or radiation therapy, or whether long-term survival of the subject, following surgery and/or termination of chemotherapy or other treatment modalities is likely. Accordingly, the present invention is also a method for selecting a therapeutic modality for the treatment of breast cancer. The method involves detecting the expression level of S14 in a sample obtained from a subject with breast cancer, comparing the level in the sample with a control, and based upon the compared level, selecting an appropriate therapeutic modality for the treatment of the breast cancer in the subject. For example, a subject with S14 levels comparable to S14 levels in breast cancer samples graded +2 may require a more aggressive treatment modality (e.g., breast cancer surgery with chemotherapy or radiation therapy), whereas a subject lacking S14 overexpression may require a less aggressive treatment modality (e.g., breast-conserving lumpectomy).

Having demonstrated that levels of S14 expression are indicative of disease-free survival, it was further determined whether S14 plays a role in breast cancer growth and survival. As SREBP-1 is a transcription factor that induces the expression of genes concerned with lipogenesis (Rawson (2003) supra), the expression of SREBP-1 in cancer cells was determined by RT-PCR analysis of hepatoma (HepG2, known to express both SREBP-1 isoforms (Shimomura, et al. (1997) *J. Clin. Invest.* 99:838-845)), lipogenic breast cancer (T47D (Chalbos, et al. (1987) *J. Biol. Chem.* 262:9923-9926)), and non-lipogenic cervical adenocarcinoma (HeLa (Oskouian (2000) *Cancer Lett.* 149:43-51)). This analysis demonstrated that both the SREBP-1a and SREBP-1c isoforms were expressed in these cell types.

It has been shown that combined androgen/progestin R1881 or progestin R5020 significantly induces S14 mRNA in T47D cells; an effect mediated by progestin as determined by by using anti-androgen CASODEX® and anti-androgen/progestin RU146 (Heemers, et al. (2000) supra). Real-time RT-PCR, using cyclophilin as a control, showed that S14, FAS, and SREBP-1c mRNAs were significantly induced by 10 nM R1881 within 48 hours. A time course using 10 nM R5020 showed induction of S14 and FAS mRNAs comparable to that observed with R1881. There was a lag time of >10 hours between application of the hormone and the onset of accumulation of S14 and FAS mRNAs. This experiment demonstrated progestin induction of SREBP-1c mRNA. As the two compounds appeared to have comparable actions in T47D cells, subsequent studies were primarily performed with R1881.

Using a human S14 gene promoter fragment fused to a luciferase reporter, the mechanism underlying R1881-induced accumulation of S14 mRNA was determined. The human S14 construct contained the proximal 4003 bp of the S14 promoter (Campbell, et al. (2003) *Endocrinol.* 144:5242-5248). This fragment does not contain a canonical progesterone response element (Lieberman, et al. (1993) *Mol. Endocrinol.* 7:515-527). Nevertheless, R1881 induced promoter activity by 4-fold. Employing a 157 bp fragment of the human FAS gene promoter that is also devoid of progesterone response elements (Swinnen, et al. (1997) supra), the effect of R1881 on FAS gene expression was examined. A 4-fold induction was observed after 48 hours exposure to the hormone, and the response from a construct with the sterol response element deleted was markedly reduced.

SREBP-1c mutants were delivered to cells via adenoviral vectors to assess the role of SREBP-1c in S14 gene activation by progestin. Cells were grown in charcoal-stripped fetal calf serum for 48 hours and infected with adenoviruses (multiplicity of infection=50) for 1 hour in the same medium. R1881 (10 nM) or vehicle was added after 8 hours, and RNA was harvested 40 hours later. S14 mRNA was induced ~8-fold in the presence of the control adenovirus (Ad-β-gal). Basal S14 expression was unaffected by the dominant-negative mutant (Ad-SREBP-1c-DN), while induction was reduced to 2.5-fold. Constitutively active SREBP-1c (Ad-SREBP1c) in the absence of R1881 caused a major induction of S14 mRNA, 330-fold over the basal value seen in the presence of Ad-β-gal without R1881, while Ad-SREBP plus R1881 superinduced, to ~1300-fold above the unstimulated level.

Western blot analysis showed effects on S14 protein concordant with those of the mRNA. Cells were grown in media containing stripped fetal calf serum for 48 hours, and then, with or without preceding adenoviral delivery of the constitutively active SREBP-1c mutant, exposed or not to 10 nM R1881 for 48 hours. No S14 was appreciable in cells cultured without hormone or Ad-SREBP-1c. A faint band of the appropriate size (~16 kD) was seen after stimulation with R1881 alone, while a strong signal appeared after exposure to Ad-SREBP-1c. As was the case for S14 mRNA, application of both stimuli induced S14 protein above the level seen with SREBP-1c alone. The adenoviral construct encoded the mature form of SREBP-1c, and thus did not require proteolytic processing. The superinduction of S14 therefore could not be ascribed to enhancement of any component of the SREBP-1c activation apparatus, such as SCAP, as was demonstrated for FAS gene expression in androgen-stimulated prostate cancer cells (Heemers, et al. (2001) supra). These data indicate that SREBP-1c is required for full induction by progestin, and also indicate the presence of an additional, SREBP-independent mechanism.

The effects of SREBP-1c and progestin on FAS expression were also analyzed. FAS mRNA was induced-2-fold by R1881 in the presence of Ad-β-gal. Basal FAS mRNA expression was slightly reduced by Ad-SREBP-1c-DN, while hormonal induction was abrogated. Ad-SREBP1c in the absence of R1881 induced FAS mRNA content to a level comparable to that seen after infection with Ad-1-gal in the presence of hormone, and Ad-SREBP plus R1881 further increased FAS mRNA accumulation. Western blot analysis using an anti-FAS antibody showed less marked induction of FAS enzyme than of S14 protein, as was the case for the respective mRNAs, but did show a clear increase in response to the combination of SREBP-1c and progestin compared to the response to either stimulus alone.

S14-related peptide (S14-RP) is ancestral to the S14 gene, and shares strong homology to three domains of S14 (Wang, et al. (2004) *Gene* 332:79-88). RT-PCR, using two different primer pairs, indicated that S14-RP transcripts occurred in T47D cells. To determine whether an anti-S14 antibody recognized S14-RP, a full-length human S14-RP cDNA (Open Biosystems, Huntsville, Ala.) with a hemagglutinin (HA) tag appended to the amino terminus was introduced into HEK293 cells by transient transfection, and western analysis was performed with anti-hS14 or anti-HA antibodies. The anti-HA blot demonstrated a band of appropriate migration (~20 kD), but no signal was observed on the blot probed with the anti-hS14 antibody. Thus, the anti-hS14 antibody does not recognize S14-RP.

In hepatocytes, induction of lipogenic gene expression requires the presence of two distinct signals, one triggered by insulin, and the other by glucose metabolism (Foretz, et al. (1999) supra). Insulin signals through SREBP-1c, and glucose metabolism is sensed by a liver-specific carbohydrate-responsive factor termed carbohydrate response element-binding protein (CHREBP) (Yamashita, et al. (2001) *Proc. Natl. Acad. Sci. USA* 98:9116-9121). Moreover, PCG-1β may directly facilitate the action of SREBP-1c in hepatocytes. To determine whether these proteins mediate superinduction of S14 gene expression by SREBP-1c and progestin, PCG-1β and CHREBP expression in T47D cells was analyzed using RT-PCR. No evidence of PGC-1β gene expression was observed. In the case of CHREBP, however, a band of the expected size was amplified from T47D cell template.

In contrast to SREBP-1 mRNA, real-time RT-PCR analysis indicated that CHREBP mRNA was not induced by progestin. A panel of five short inhibitory RNAs (siRNAs) were assessed for inhibition of CHREBP expression. None were effective in reducing levels of CHREBP mRNA, including an siRNA corresponding to the human homolog (5'-tac gtc ggc aat gct gac at-3', SEQ ID NO:2) of a mouse sequence which has been successfully used to reduce levels of mouse CHREBP (5'-tat gtt ggc aat gct gac at-3', SEQ ID NO:3) (Dentin, et al. (2004) *J. Biol. Chem.* 279:20314-20326).

There has been an indication that progestin induces glucose transporter expression in lipogenic ZR-75-1 human breast cancer cells, suggesting a link between sex steroids and glucose in lipogenic gene regulation in breast cancer cells (Medina, et al. (2003) *Endocrinology* 144:4527-4535). While CHREBP mRNA was readily detectable in T47D breast cancer cells, no major induction of S14 or FAS mRNAs was observed in response to increasing the glucose concentration in culture media from 5.5 to 27 mM, a stimulus that is sufficient for maximal induction of lipogenesis-related genes in hepatocytes (Foretz, et al. (1999) *Mol. Cell. Biol.* 19:3760-3768). To assess the potential role of glucose signaling in lipogenic gene regulation in T47D cells, cells were acclimatized for 3 days to media containing 5.5 mM glucose and stripped fetal calf serum. Subsequently some wells were switched to high-glucose medium (27 mM) with or without 10 nM R1881 for 48 hours. Analysis of S14 mRNA by real-time RT-PCR revealed only minor induction by glucose, which in the presence of hormone was not statistically significant. Thus, glucose signaling through CHREBP does not appear to mediate the S14 superinduction.

Enforced overexpression of S14 was achieved by infecting cells with adenovirus harboring a full-length rat S14 cDNA. Using an antibody specific for rat S14, western blot analysis of cell lysates collected 3 days after adenoviral infection revealed no signal from cells infected with control adenovirus (Ad-β-gal), or an adenovirus harboring the S14 cDNA in the antisense orientation. Infection with Ad-rS14, however, yielded a strong band of the appropriate size (~17 kD), of intensity comparable to that observed in liver from a hyperthyroid rat fed a fat-free, high carbohydrate diet. Infection with Ad-rS14 accelerated accumulation of viable cells by 45% above that observed after infection with Ad-β-gal after 5 days. Similar effects were observed in MCF7 and SKBR3 breast cancer, but not MCF10a mammary epithelial or HepG2 hepatocarcinoma cells.

To reduce S14 mRNA and protein expression, siRNA targeting S14 were employed. T47D cells were difficult to transfect with siRNA, owing to variable transfection efficiency between experiments. The cause of the variability was not clear, except that highly passaged cells appeared less susceptible to transfection. Using low passage number cells (<8), fluorescent-tagged siRNA (f1-siRNA) were transfected in each experiment. Four hours after transfection, FACS analysis was conducted to monitor transfection efficiency. Only experiments with transfection efficiency>80% were analyzed further. Cells were scrutinized by laser confocal microscopy 4 hours after transfection of f1-siRNA to assure that the siRNA was inside, rather than on the surface of, the cells at that time point. Cell transfected with f1-siRNA exhibited a diffuse intracellular signal, rather than a surface pattern. Several siRNAs were assessed and two were found to be effective in experiments with adequate transfection efficiency (>90%). Real-Time RT-PCR and western analysis of cell lysates at 48 hours post-transfection demonstrated that siRNA knocked down S14 protein levels and mRNA levels (mRNA levels were ~10-25% of controls). Cyclophilin mRNA was employed as a reference sequence, and did not vary among treatments.

Having demonstrated effective reduction in S14 levels using siRNA, two aspects of S14 action in breast cancer cells were assessed. The effect of siRNA on T47D viable cell accumulation over time was determined. Cells accumulated in the presence of the control siRNA, whereas significant cell dropout was observed in the presence of the siRNA. A comparable effect was observed with another S14-siRNA. It was also determined whether a reduction in S14 expression would abrogate the induction of FAS mRNA by progestin. Real-time RT-PCR analysis using FAS-specific primers demonstrated a significant reduction in FAS message in response to S14 siRNAs within 48 hours post-transfection.

The effect of adenovirus harboring S14 cDNA in the antisense orientation was also examined to determine if the effect of siRNA on T47D cell growth would be observed when using this alternative technique. Growth of cells exposed to the control virus did not differ from the uninfected group 120 hours after infection. Inspection showed that a major cell dropout began in the Ad-S14-AS group 72-96 hours after infection, and this was confirmed by MTS assay. Lipid synthetic rate of the cells before the onset of apoptosis (48 and 72 hours post-infection, respectively) was also examined. Incorporation of labeled acetate into lipids was not different among the groups 48 hours post-infection, whereas a sharp reduction was seen in antisense-treated wells 24 hours later. An in situ TUNEL assay 96 hours post-infection showed evidence of apoptosis in the antisense-treated group. Apoptotic effects of Ad-S14-AS were also seen in MCF7 and SKBR3 breast cancer cells, whereas the antisense adenovirus had no effect on the accumulation of HepG2 cells.

Analogous studies were performed using siRNA transfection in MCF10a cells, a non-tumorigenic human mammary epithelial line that expresses low levels of lipogenic enzymes and is not susceptible to killing by FAS enzyme inhibition as are transformed MCF10a or breast cancer cell lines (Yang, et al. (2002) *Exp. Cell Res.* 279:80-90). FACS analysis 4 hours after transfection using fluorescent siRNA showed that MCF10a cells were transfectable. T47D and MCF10a cell content of S14 and FAS mRNAs were compared and levels of both messages were so low that some wells yielded no signal. In contrast to T47D cells, MCF10a cell growth was not affected by S14 siRNA. To further compare the phenotypes of the T47D and MCF10a cells, both cell lines were exposed to the fatty acid synthase inhibitor cerulenin (10 μg/mL for 48 hours). This confirmed previous reports of the differential sensitivity of the lines to inhibition of lipogenesis (Pizer, et al. (1996) supra; Yang, et al. (2002) supra).

The data disclosed herein demonstrated FAS and S14 gene induction by progestin in breast cancer cells (Joyeux, et al. (1989) *Mol. Endocrinol.* 4:681-686; Heemers, et al. (2000) supra). Similarly SREBP-1c mRNA was increased by the steroid as well. SREBP-1c gene expression has been shown to be inducible in other circumstances, including stimulation by insulin and high glucose in rat hepatocytes (Foretz, et al. (1999) supra), by refeeding in mouse liver and adipocytes (Kim, et al. (1998) *J. Clin. Invest.* 101:1-9), and by androgen in prostate cancer cells (Heemers, et al. (2001) supra). States of increased SREBP-1c action result in enhanced turnover of the extranuclear precursor (Yabe, et al. (2003) *Proc. Natl. Acad. Sci. USA* 100:3155-3160), and augmented production is required to maintain an activated steady-state. Inhibition of SREBP-1c was found to reduce the capacity of progestin to enhance S14 and FAS mRNA expression, thus providing direct evidence for its requirement in the action of the hormone in breast cancer cells. Abrogation of progestin-induced FAS reporter gene activity in the construct lacking the sterol response element was consistent with this. Conversely, a constitutively active SREBP-1c mutant increased expression of the endogenous S14 and FAS genes in T47D breast cancer cells in the absence or presence of progestin. In the presence of hormone, striking superinduction of both mRNAs was observed with concurrent SREBP-1c stimulation. Moreover, increased and reduced S14 protein expression effected concordant changes in the growth of breast cancer cells. Therefore S14 and associated components of the lipid synthetic pathway in breast tumors are useful as therapeutic targets for the prevention and treatment of breast cancer.

Accordingly, the present invention is also a method for treating breast cancer in a subject having or at risk of having breast cancer. A subject having or suspected of having breast cancer may exhibit one or more of the typical signs or symptoms associated with the disease including a lump, an area of thickening, or a dimple in the breast or the less common signs include breast swelling and redness or an enlarged underarm lymph node. Subjects at risk of having breast cancer include those with a family member or family history of having breast cancer or who have inherited an abnormal breast cancer gene.

A subject having or at risk of having a breast cancer is administered an effective amount of an agent that inhibits the expression or activity of S14 (i.e., an S14 inhibitor) thereby inducing apoptosis in breast cancer cells and having a beneficial or desired clinical result. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. Treatment can also mean prolonging survival as compared to expected survival if not receiving treatment. As will be understood by the skilled artisan, the signs or symptoms of the breast cancer can vary with the stage of the cancer and the signs or symptoms associated with various stages are well-known to the skilled clinician. See, for example, The American Joint Committee on Cancer Staging Manual, Sixth Edition.

An effective amount of an agent that inhibits the expression or activity of S14 is an amount sufficient to induce apoptosis in breast cancer cells and effect beneficial or desired results, including clinical results. A reduction or decrease in S14 expression or activity is intended to mean a 30%, 40%, 50%, 60%, 70%, 80%, 90%, 95%, 98%, or 100% decrease in expression or activity when compared to otherwise same conditions wherein an S14 inhibitor is not present. As a result of such a decrease in S14 expression or activity, apoptosis is induced in breast cancer cells of the subject thereby preventing, eliminating, stabilizing or alleviating one or more signs or symptoms of a breast cancer. Such a decrease in the expression or activity of S14 will be dependent on the subject and the condition of the subject, the mode of administration of the agent, the stage of the cancer being prevented or treated and the particular agent being employed.

As demonstrated herein, S14 inhibitors promote apoptotic cell death. Accordingly, the present invention also relates to a method for using S14 inhibitors to modulate the growth of a breast cancer cell either in vitro or in vivo. The method involves contacting a breast cancer cell with an effective amount of an S14 inhibitor (i.e., an agent that inhibits the expression or activity of S14) so that apoptosis of said cell is induced or promoted. Induction or promotion of apoptosis of a breast cancer cell is intended to mean a 30%, 40%, 50%, 60%, 70%, 80%, 90%, 95%, 98%, or 100% increase in cell death when compared to otherwise same conditions wherein the S14 inhibitor is not present. Measurements of cell death can be performed using methods well-known to those of skill in the art, e.g., measuring a reduction in tumor size, an decrease in cell number or the expression of apoptosis marker proteins (e.g., caspases).

In particular embodiments, the S14 inhibitor is an siRNA (e.g., targeting nucleic acids set forth in SEQ ID NO:4 or SEQ ID NO:5) or an antisense molecule (e.g., an antisense molecule of a nucleic acid encoding a protein set forth in SEQ ID NO:1).

For use in accordance with the present invention, an S14 inhibitor can generally be formulated into a pharmaceutical composition for administration to human subjects in a biologically compatible form suitable for administration in vivo. A pharmaceutical composition containing an S14 inhibitor can be prepared by known methods for the preparation of pharmaceutically acceptable compositions which can be administered to subjects, such that an effective amount of the active substance is combined in a mixture with a pharmaceutically acceptable vehicle. Generally, a pharmaceutical composition contains, for example, 0.1 to 99.5%, or more suitably 0.5 to 90%, of active ingredient in combination with a pharmaceutically acceptable vehicle. Suitable vehicles are described, for example, in Remington: The Science and Practice of Pharmacy, Alfonso R. Gennaro, editor, 20th ed. Lippincott Williams & Wilkins: Philadelphia, Pa., 2000. Such compositions include, albeit not exclusively, solutions of an S14 inhibitor in association with one or more pharmaceutically acceptable vehicles or diluents, and contained in buffered solutions with a suitable pH and iso-osmotic with the physiological fluids.

An S14 inhibitor can be used in accordance with the method of the present invention in the form of a salt, solvate or as hydrate. All forms are within the scope of the invention.

In accordance with the methods of the invention, an S14 inhibitor can be administered to a subject in a variety of forms depending on the selected route of administration, as will be understood by those skilled in the art. An S14 inhibitor can be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

An S14 inhibitor can be orally administered, for example, with an inert diluent or with an assimilable edible carder, or it can be enclosed in hard or soft shell gelatin capsules, or it can be compressed into tablets, or it can be incorporated directly with the food of the diet. For oral therapeutic administration, an S14 inhibitor can be incorporated with an excipient and used in the form of ingestible tablets, buccal tablets, troches, capsules, elixirs, suspensions, syrups, wafers, and the like.

An S14 inhibitor can also be administered parenterally. Solutions of an S14 inhibitor can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations using conventional procedures and ingredients for the selection and preparation of suitable formulations.

Pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration can conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container can be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine.

An S14 inhibitor can be administered to a subject alone or in combination with pharmaceutically acceptable carriers, as noted above, the proportion of which is determined by the solubility and chemical nature of the inhibitory agent, chosen route of administration and standard pharmaceutical practice.

The dosage of an S14 inhibitor can vary depending on many factors such as the mode of administration, the age, health and weight of the recipient, the nature and extent of the symptoms, the frequency of the treatment and the type of concurrent treatment, if any and the clearance rate of the compound in the subject to be treated. One of skill in the art can determine the appropriate dosage based on the above factors. An S14 inhibitor can be administered initially in a suitable dosage that can be adjusted as required, depending on the clinical response.

Actual dosage levels and time course of administration of an S14 inhibitor in a pharmaceutical composition can vary so as to obtain an amount of an S14 inhibitor which is effective to achieve the desired therapeutic response for a particular subject and mode of administration, without being toxic to the subject.

An S14 inhibitor can be used alone or in combination with a second anticancer agent. For example, an S14 inhibitor can be administered in combination with calcitriol or other vitamin D receptor agonists. Other treatments which can be combined with the use of an S14 inhibitor include, but are not limited to, Doxorubicin, Paclitaxel, Methotrexate, 5-Fluorouracil, Docetaxel, Thiotepa, Cisplatin, Estrogen receptor modulators such as Tamoxifen and Toremifene, Estrogens (e.g., diethylstilbestrol), Androgens (e.g., fluoxymesterone), Gonadotropin-Releasing Hormone (GnRH), Anastrozole, Aromatase inhibitors (antineoplastics), Vinorelbine tartrate, Gemcitabine hydrochloride, Progestins (e.g., Medroxyprogesterone acetate, Megestrole acetate), Trastuzumab (HERCEPTIN®), or Cyclophosphamide.

An S14 inhibitor can be administered prior to the administration of the second agent, simultaneously with the second agent, or after the administration of the second agent. Furthermore, an S14 inhibitor can be administered in a proform which is converted into its active metabolite, or more active metabolite in vivo.

As indicated, a S14 inhibitor is intended to include an agent that inhibits the activity or expression of S14. Such agents include those disclosed herein as well as other agents identified in screening assays for agents that inhibit the expression or activity of S14. Agents of the invention can be ligands or antibodies that bind to S14, agents that prevent nuclear localization of S14, agents that block multimerization of S14, or agents that block transcription or replication of S14 DNA or translation of S14 mRNA. Agents can be proteins or fragments thereof, small molecules, or nucleic acid molecules.

Various commercial sources are well-known in the art for providing small molecule libraries for the identification of useful compounds. Screening of such libraries of test compounds, including combinatorially generated libraries (e.g., peptide libraries), is a rapid and efficient way to screen large numbers of related (and unrelated) compounds for S14 inhibitory activity. Combinatorial approaches also lend themselves to rapid evolution of potential drugs by the creation of second, third and fourth generation compounds modeled of active, but otherwise undesirable compounds.

Test agents can include fragments or parts of naturally-occurring compounds, or may be found as active combinations of known compounds, which are otherwise inactive. It is contemplated that compounds isolated from natural sources, such as animals, bacteria, fungi, plant sources, including leaves and bark, and marine samples can be assayed as test agents for the presence of potentially useful pharmaceutical agents. It will be understood that the test agents to be screened could also be derived or synthesized from chemical compositions or man-made compounds. Thus, it is understood that the test agent identified by the present invention can be peptide, polypeptide, polynucleotide, small molecule inhibitors or any other compounds that can be screened for or designed through rational drug design.

Other suitable S14 inhibitors include siRNA molecules, antisense molecules, ribozymes, and antibodies (including single chain antibodies), each of which would be specific for the target S14 molecule. Examples of such agents are described herein. For example, an antisense molecule that binds to a translational or transcriptional start site, or splice junction, would be an ideal S14 inhibitors.

An inhibitor according to the present invention can be one which exerts its inhibitory effect upstream, downstream or directly on S14 nucleic acid or protein. Regardless of the type of inhibitor identified by the present screening methods, the effect of the inhibition by such an agent results in reduction in the expression or activity of S14 as compared to that observed in the absence of the added inhibitor agent.

An inexpensive and easy assay for identifying S14 inhibitors is an in vitro assay. Such assays generally use isolated molecules, can be run quickly and in large numbers, thereby increasing the amount of information obtainable in a short period of time. A variety of vessels can be used to run the assays, including test tubes, plates, dishes and other surfaces such as dipsticks or beads.

One example of a cell-free assay is a binding assay. While not directly addressing function, the ability of an inhibitor to bind to a target molecule in a specific fashion is strong evidence of a related biological effect. For example, binding of a molecule to a target can, in and of itself, be inhibitory, due to steric, allosteric or charge-charge interactions. The target can be either free in solution, fixed to a support, expressed in or on the surface of a cell. Either the target or the compound can be labeled, thereby permitting determining of binding. Usually, the target will be the labeled species, decreasing the chance that the labeling will interfere with or enhance binding. Competitive binding formats can be performed in which one of the agents is labeled, and one can measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

In a yeast two-hybrid assay using S14 as bait (Cunningham, et al. (1997) *Endocrinol.* 138:5184-5188), approximately 100 strongly interacting clones were identified, all of which were S14 cDNAs. This analysis indicated that S14 formed multimers. The relevance of the S14-self interaction in the yeast two-hybrid system to mammalian cells was verified by co-transfecting S14 constructs bearing two different tags, and demonstrating that HA-tagged S14 co-purified with GST-S14, but not GST, on glutathione affinity chromatography (Cunningham (1997) supra). Analysis of deletion mutants in yeast indicated that the C-terminal "zipper domain" of S14, which is predicted to be alpha-helical, was required for multimer assembly. In addition, screening a cDNA library devoid of S14 (HeLa cell, as assessed by RT-PCR), screening with S14 bait lacking the zipper domain, and digesting the cDNA library with a rare-cutting restriction enzyme that cleaves the S14 sequence did not yield additional binding partners.

Analytical equilibrium ultracentrifugation and light-scattering indicated that S14 forms a homotetramer in solution. Secondary structure prediction software (Jpred) identified 20 residues in S14 domain III with the potential to form a coiled-coil, typical of an oligomerization motif. Circular dichroism experiments using a 20-mer representing residues 120-139 of that domain showed a peak at 190, and a nadir at 210 nM, typical of an $\alpha$-helix, in 50% trifluoroethanol (i.e., Cotton effect). In contrast to complete S14, the 20-mer was small enough for NMR spectroscopy. NMR data verified the helical configuration, and disclosed that the helices interact in parallel. Modeling as a four parallel helix bundle predicted several residues, particularly Tyr138 of SEQ ID NO:1, to be key for stabilizing the tetrameric interface. A Tyr138Ala S14 mutant was expressed in bacteria and, in contrast to wild-type S14, was not found in the soluble fraction. Western blot analysis confirmed that the mutant was confined to the insoluble cell pellet, indicating that Tyr138 is a crucial residue for assembly of soluble S14 tetramers.

These data demonstrate that S14 forms multimers in vitro and in vivo, and that it interacts with 140 and 10 kD peptides in breast cancer cells. Domain III is demonstrated to be helical in solution, where it forms a tetramer in parallel orientation. Moreover, within Domain III Tyr138 is a vulnerable point in assembly of tetrameric S14. Of note, Tyr138 is conserved in S14 and S14-RP homologs from zebrafish to humans (Wang, et al. (2004) *Gene* 332:79-88).

Accordingly, particular embodiments of the present invention embrace in vitro assays for identifying a test agent that decreases the multimerization of S14 thereby blocking activity of S14. In accordance with such an assay, S14 is contacted with a test agent and multimerization is determined, e.g., by detecting soluble multimers of S14 via western blot analysis. Agents that block multimerization of S14 are useful for inducing apoptosis in a breast cancer cell and in the treatment of breast cancer.

Moreover, it is contemplated that given the importance of Tyr138 for multimerization, the step of determining the multimerization of Spot 14 can be carried out by computer modeling using docking programs such as GRAM, DOCK, or AUTODOCK to identify agents which interact with Tyr138 thereby interfering with multimerization. Computer programs can be employed to estimate the attraction, repulsion, and steric hindrance of a compound to Tyr138. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with other proteins thereby minimizing potential side-effects.

The present invention also contemplates the screening of compounds for their ability to inhibit S14 expression or activity in cells. Various cell lines can be utilized for such screening assays, including cells specifically engineered for this purpose. For example, cells containing S14 regulatory elements (e.g., promoter) operatively linked to a reporter molecule are specifically contemplated for use in identifying agents that inhibit the expression of S14. Depending on the assay, cells can be examined for different physiologic phenotypes (e.g., induction of apoptosis) or, alternatively, molecular analysis can be performed, for example, looking at protein expression, mRNA expression (including differential display of whole cell or polyA RNA) and others.

In vivo assays can involve the use of various cell or animal models, including transgenic animals that have been engineered, e.g., to carry markers that can be used to measure the ability of a test agent to effect the expression or activity of S14. In such assays, one or more test agents are contacted with a cell, and the ability of the test agent(s) to inhibit the expression or activity of S14, as compared to a similar cell not treated with the test agent(s), is determined. Determination can be achieved by detecting the binding of ligands or antibodies to S14, detecting nuclear localization of S14, detecting multimerization of S14, or detecting transcription or replication of S14 DNA or translation of S14 mRNA.

For example, agents that inhibit the transcription or translation of S14 can be identified by employing nucleic acids encoding a reporter (e.g., GFP or luciferase) operably linked to the S14 promoter (and 5' and/or 3' untranslated regions; see Campbell, et al. (2003) supra), wherein the presence of the reporter in a cell is indicative of the transcription and translation of S14. As such, an agent that decreases the presence or level of the reporter in the test cell when compared to a test cell not contacted with the agent, indicates that the agent decreases the presence or level of S14 and is therefore useful for inducing or promoting apoptosis in breast cancer cells. Such cell-based reporter assays are routinely carried out by the skilled artisan with more detail discussed in Zysk (1998) *Comb. Chem. High Throughput Screen* 1(4):171-83 and Gonzalez et al. (1998) *Curr. Opin. Biotechnol.* 9(6):624-31.

Agents identified in accordance with the methods disclosed herein are useful in inducing apoptosis in breast cancer cells and in the treatment of breast cancer.

The following non-limiting examples are presented to better illustrate the invention.

Example 1

Patient Population

From a database of 700 patients with blinded demographic information on tumor characteristics, including size, histological grade, lymph node status, and expression of conventional tumor markers (e.g., estrogen receptor, progesterone receptor, and Her2/neu) was selected 132 tumors. Of the selected tumors, 44 were consecutive cases of DCIS, 34 were consecutive cases of node (−) breast cancer, 54 were consecutive cases of node (+) breast cancer and 20 were mammary gland samples from women undergoing reduction mammoplasty who had no history of breast cancer (10 pre- and 10 post-menopausal).

Example 2

Determination of Conventional Tumor Markers

Immunostaining of tumor cell nuclei for estrogen receptor and progesterone receptor expression was defined as "negative" (no immunostaining); "equivocal" (1-15% tumor cell nuclei staining); and "positive" (>15% tumor cell nuclei staining). C-erb-B2 surface protein expression was scored immunohistochemically as 0 through 3+, according to adapted criteria defined in the HERCEPTEST. Score 0 was defined as absent or faint membranous immunostaining in <33% of the tumor cells. Score 1+ was defined as barely perceptible partial membranous staining in >33% of the tumor cells. Score 2+ was defined as weak to moderate staining of the entire cell membrane in >33% of the tumor cells. Score 3+ was defined as strong staining of the entire cell membrane in >90% of the tumor cells. Scores of 0, 1+ and 2+ were deemed as negative, and scores of 3+ to indicate overexpression. Her2neu slides were read by one experienced pathologist and the rate of cases scored as 2+ that exhibited a positive signal by fluorescent in situ hybridization (FISH) was 2.5%. In view of cost of that test and the excellent reproducibility of immunohistochemical analysis for this antigen, cases graded as 2+ by FISH were not routinely analyzed.

Example 3

Anti-Human S14 Antibody Production

A monoclonal antibody selected for specifically binding to a S14 protein of SEQ ID NO:1 in breast tissue or cells was prepared by generating hybridomas from splenocytes of mice immunized with glutathione-S-transferase (GST)-tagged human S14 expressed from vector pGEX-3× (Amersham, Piscataway, N.J.) in E. coli. Female Balb/C mice were immunized intraperitoneally with 50 µg GST-S14 mixed in RIBI adjuvant (Sigma, St. Louis, Mo.), and boosted with 20 µg antigen in adjuvant 3 and 6 weeks later. Splenocytes were fused with NS1 cells (ATCC, Manassas, Va.) 4 days later. Screening was by ELISA using wells coated with His6-tagged S14 expressed in bacteria from vector PROEX-HT (Life Technologies, Gaithersburg, Md.). Crude supernatant (1:1000 dilution of hybridoma "KVB7", an IG2a) or anti-HA (Sigma, St. Louis, Mo.) were used in western analysis with protein A-alkaline phosphatase conjugate for detection of S14 or HA-tagged S14-related peptide, respectively, as described (Kinlaw, et al. (1992) supra).

Example 4

Immunohistochemistry

Tissues were fixed in 10% buffered formalin (Biochemical Science Inc, Swedesboro, N.J.), dehydrated through graded alcohols, and paraffin embedded. Tissue sections (4 µm) were coated with adhesive (STA-ON; Surgipath Medical Industries, Inc, Richmond Ill.), mounted on glass slides and stained with hematoxylin for initial review. Estrogen receptor protein and progesterone receptor protein expression (1:10 and 1:40, respectively; Biogenix, San Ramon, Calif. with Citra Plus antigen retrieval) and C-erb-B2 surface protein expression (1:20; Biogenix, San Ramon, Calif. with Citra antigen retrieval) were assessed immunohistochemically in the clinical laboratory at the time of diagnosis. S14 was detected with crude supernatant from a hybridoma designated K/IIIC5.1, which produces anti-S14 antibody, an IG2a. FAS was detected with an affinity-purified rabbit anti-human FAS IgG preparation, (Immuno-Biological Laboratories Co., Gunma, Japan) 1:100 at 3 µg/mL. Cyclin D1 was detected with the mouse monoclonal, 1:100 (Biocare, Walnut Creek, Calif.) with Borg antigen retrieval according to published data (Petty, et al. (2004) supra). Tissue sections were cut, deparaffinized with xylene and hydrated through graded alcohols. Sections were mounted on Biogenix Plus slides (San Ramon, Calif.) and epitope retrieval was carried out in a steamer under pressure, using Citra, Citra Plus or Borg antigen retrieval buffers (Biogenix, San Ramon, Calif.). Slides were rinsed in distilled water, soaked in phosphate-buffered saline and immunostained in a BioGenix I-6000 autostainer (San Ramon, Calif.) using the Biotin-Streptavidin Amplified system, with identical timing of incubations and washes for all cases. Diaminobenzidine was applied for visualization. Slides were counterstained with hematoxylin, dehydrated through graded alcohols and coverslipped with Richard Allen mounting medium (Richard Allen Medical, Richland, Mich.).

Example 5

Determination of S14, FAS and Cyclin D1 Levels

All immunoslides were semi-quantitatively scored by one Pathologist. For each antibody, 20 randomly chosen cases were reviewed by a second pathologist to confirm immunoscoring reproducibility. S14 and FAS were scored 0 through 2+ according to the intensity of immunostaining (nuclear for S14, cytoplasmic for FAS). Semi-quantitative analysis for the determination of marker levels by immunohistochemical analysis is well-known in the art. See, for example, Petty, et al. (2004) Clin. Canc. Res. 10:7547-7554. In accordance with established methods, score 0 was defined as no immunostaining; score 1+ was defined as weak, diffuse immunostaining; score 2+ was defined as strong, diffuse immunostaining. Cyclin D1 was scored 0 through 3+ according to the percentage of tumor nuclei staining (irrespective of the intensity) using published data (Petty, et al. (2004) supra) as follows: score 0 was defined as no immunostaining; score 1+ was defined as <25% of tumor cell nuclei staining; score 2+ as 25-75% of tumor cell nuclei staining; score 3+ as >75% of tumor cell nuclei staining.

Example 6

Statistical Analyses of Clinical Data

Confidence intervals for rates were calculated using exact binomial methods. Comparisons for S14 and cyclin D1 overexpression between groups were performed using Fisher's exact test. Time to disease recurrence between groups was compared using Kaplan-Meier survival estimates and the log-rank test. Proportional hazards regression was also used to jointly examine the influence of the stage, prognostic factors, and S14 overexpression on the time to recurrence.

Example 7

S14 as a Prognostic Marker for Breast Cancer

To demonstrate that S14 is a marker for breast cancer, the presence of S14 in breast tissues was initially analyzed using a commercially available antibody preparation to S14; however, this antibody preparation was not sufficient for detecting differential expression of S14 in breast tissue. Accordingly, a monoclonal antibody selected for specifically binding to S14 in breast tissue was generated. To analyze the specificity of the S14 monoclonal antibody, western blot analysis of T47D human breast cancer cells was performed. To increase expression of S14 in these cells, either a progestin (10 nM R5020) (Heemers, et al. (2000) *Biochem. Biophys. Res. Commun.* 269:209-212) or adenovirally-delivered sterol response element-binding protein-1c (SREBP-1), a transcription factor that induces the expression of genes concerned with lipogenesis (Rawson (2003) *Nat. Rev. Mol. Cell. Biol.* 4:631-6) was applied as a stimulus. To decrease expression of S14, T47D human breast cancer cells were exposed to an S14 short inhibitory RNA. In each instance, a single S14 band of appropriate mobility (~16 kD) was observed, the intensity of which was concordant with the level of S14 mRNA.

Resting and lactating human mammary gland were also examined for S14 expression using the S14-specific monoclonal antibody in immunohistochemistry; lactation is a major stimulus for S14 expression in epithelium of the lobuloalveolar units (Moncur, et al. (1998) supra). Resting mammary showed primarily white adipocytes of the fat pad with strong nuclear and some cytoplasmic staining, whereas the lactiferous duct epithelium was essentially devoid of S14. Lactating mammary gland showed strong staining in nuclei and cytoplasm of the epithelial cells, whereas staining for FAS showed an intense cytoplasmic signal, with sparing of the nuclei.

Further, immunohistochemical analysis of breast cancer was conducted using the S14-specific monoclonal antibody. Both ductal carcinoma in situ (DCIS), a form of non-invasive breast cancer, and invasive breast cancer tissues were stained for S14 and FAS. As observed in rat liver (Kinlaw, et al. (1989) *J. Biol. Chem.* 264:19779-19783) and breast cancer (Moncur, et al. (1998) supra) using polyclonal IgG preparations in immunohistochemistry, the S14-specific antibody primarily stained the nucleus. FAS immunoreactivity was cytosolic, as expected (Jensen, et al. (1995) *J. Pathol.* 176: 343-352). Tumors of either type yielded no signal when primary antibodies were omitted.

Having established the presence of both S14 and FAS in breast cancer tissue, the frequency of S14 and FAS expression in normal and malignant mammary tissue was examined. Of the 132 cases analyzed, S14 and FAS were detectable in essentially all examples of normal mammary gland, DCIS, and invasive breast cancer (Table 1). The frequency of maximal expression did not vary between DCIS and invasive cancers, and the scores did not differ between invasive cancers with (34 cases) and those without (54 cases) lymph node metastases.

TABLE 1

| Tissue (n) | S14 Staining (%) | FAS Staining (%) |
|---|---|---|
| DCIS (44) | | |
| Detectable | 97 | 97 |
| Maximal | 68 | 97 |
| Invasive breast cancer (88) | | |
| Detectable | 99 | 99 |
| Maximal | 76 | 97 |
| Normal mammary (20) | | |
| Detectable | 100 | 100 |
| Maximal | 60 | 70 |

The detectable category for S14 or FAS refers to an immunohistochemical score of 1 or 2; the maximal category corresponds to scores of 2. The normal mammary gland group included samples from 10 pre- and 10 post-menopausal women. The data were pooled because there was no significant difference in staining intensities between them.

The fraction of cases exhibiting maximal staining for S14, but not FAS, was significantly correlated with tumor grade and size (FIG. 1). S14 expression in grade 1 DCIS was as likely to be maximal as it was in normal mammary epithelium (FIG. 1, Panel A), but the prevalence of strong staining increased with advancing grade, to 97% in grade 3 cases ($p=0.003$). In invasive cancers (FIG. 1, Panel B) a similar relationship was found, with 100% of grade 3 tumors (pooled lymph node negative and positive) exhibiting a maximal signal ($p<0.001$). Invasive cancers also exhibited increased S14 expression as a function of tumor size (FIG. 1, Panel C). Strong staining was found in 58% of tumors<1.0 cm in size, and increased to 80% and 83% for lesions 1.0-2.0 and >2.0 cm in diameter, respectively ($p=0.05$). The number of cases at each S14 score precluded multivariate analysis, but there did appear to be an effect of tumor grade independent of the S14 score. Among strongly staining-cases, none of 11 grade 1 invasive tumors recurred, 2/19 grade 2 tumors recurred, and 12/26 grade 3 tumors recurred.

In DCIS, the relationship between FAS expression and tumor grade nearly reached significance, with grade 1/2/3 cases exhibiting maximal expression in 86/96/100% of cases, respectively ($p=0.076$). This is consistent with a previous report (Milgraum, et al. (1997) *Clin. Canc. Res.* 3:2115-2120). No such relationship was observed in invasive cases, because all samples exhibited maximal expression of this antigen. As with S14, FAS content in the tumor correlated with invasive tumor size. Strong staining was found in 88% of tumors<1.0 cm in size, and increased to 100% for 1.0-2.0 or >2.0 cm lesions ($p=0.036$).

In a comparison of the expression of S14, FAS, and conventional tumor markers, there was no significant correlation between the expression of S14 and estrogen receptor or progesterone receptor status in either DCIS or invasive cases. Likewise, there was no association of a positive score for Her2/neu with the S14 or FAS scores. However, Her2/neu amplification did adversely affect disease-free survival ($p=0.046$).

In both DCIS and invasive breast cancer there was no observed relationship between the S14 score and the level of cyclin D1 expression ($p=1.00$ and $0.28$, respectively), an art-recognized mammary oncogene (Hinds, et al. (1994) *Proc. Natl. Acad. Sci. USA* 91:709-713). Cyclin D1 staining was significantly enhanced in DCIS and invasive cancer compared to normal mammary epithelium, but did not correlate with tumor size at either stage ($p=0.42$ and $p=0.25$, respectively). Likewise, Cyclin D1 staining did not correlate with tumor grade in either DCIS or invasive disease. In DCIS, strong staining for cyclin D1 was associated with estrogen receptor expression (p=0.028). The association of cyclin D1 expression and that of progesterone receptor was also statistically significant (p=0.05). In invasive cases, the association between progesterone receptor and strong cyclin D1 expression nearly reached significance (p=0.058). However, no association was found between the cyclin D1 score and disease-free survival (p=0.4).

Figure 2:
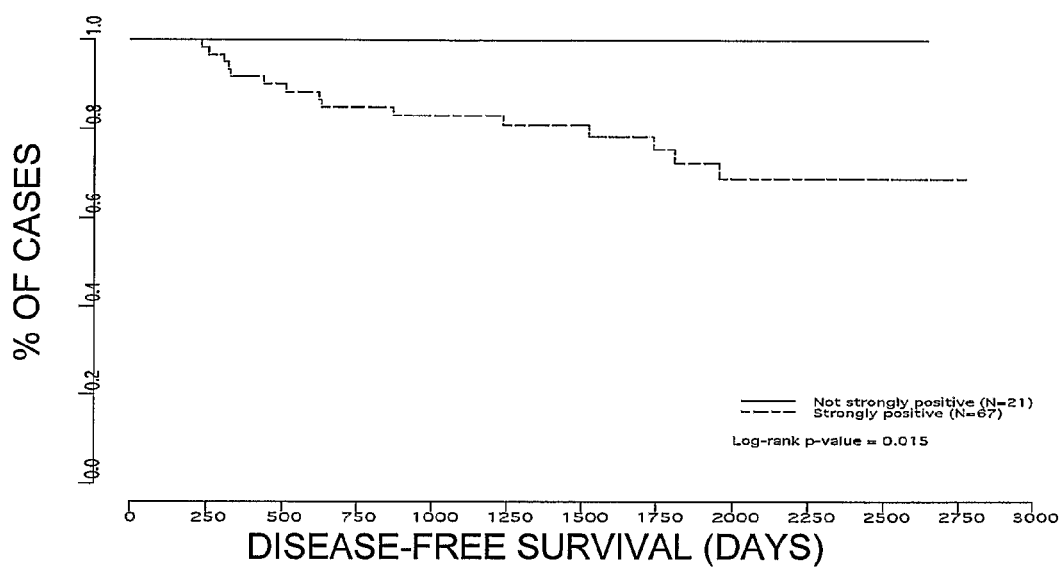
FIG. 2 shows the disease-free survival of subjects after treatment of invasive breast cancer as a function of S14 expression in the primary tumor. Subjects with and without positive lymph nodes at initial surgery were pooled for Kaplan-Meier analysis. Those with an immunohistochemical score of 0 or 1+ (n=21) are represented by the solid line, and those with a 2+ S14 score by the dotted line (n=67). The difference between the two plots was statistically significant (p=0.015).

Kaplan-Meier analysis of recurrence after primary treatment of initially invasive tumors, with or without lymph node involvement at the time of surgery, revealed a significant relationship (p=0.015) between the level of S14 expression in the primary tumor and disease-free survival over the ensuing 3000 days (FIG. 2). No cases exhibiting a score of 0 or 1+ (n=21) recurred, whereas 32% of tumors with maximal S14 content recurred (n=67).

Figure 3:
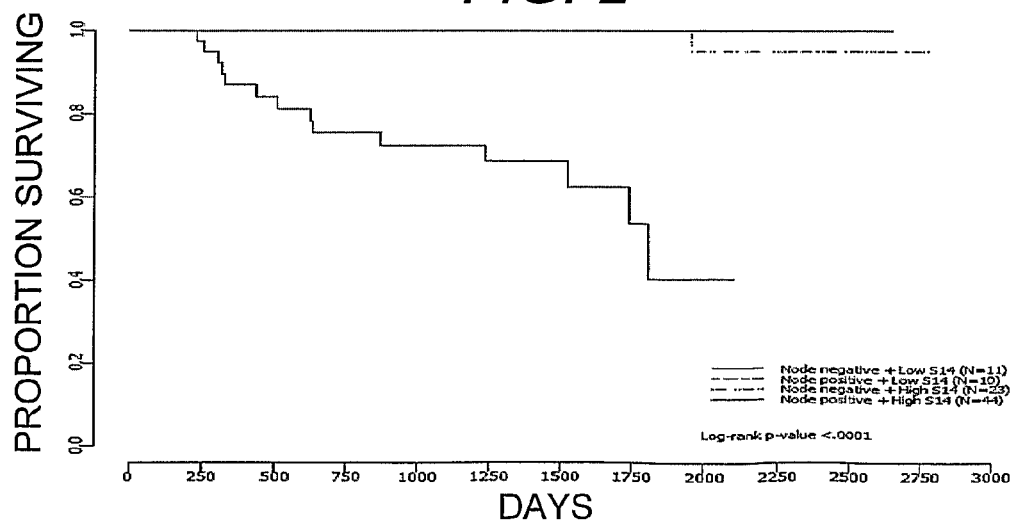
FIG. 3 shows disease-free survival in subjects with invasive breast cancer as a function of S14 scores and the presence or absence of lymph node metastases at initial surgery. The same subjects represented in FIG. 2 were analyzed by Kaplan-Meier analysis. Subjects with negative lymph nodes and submaximal S14 scores (n=11) or positive lymph nodes and low S14 scores (n=10) are represented by the top tracings, which are superimposed. There were no recurrences in those groups. Among subjects with negative lymph nodes and a high S14 scores (n=23), one recurred after ~2000 days follow-up (dashed line). Among the subjects with nodal metastasis and strong S14 staining (n=44), there were 14 recurrences (p<0.0001).

Separable effects of S14 and the presence of nodal metastases at initial surgery were observed on disease-free survival in invasive disease (FIG. 3). Among 34 node-negative cases, only one recurrence was seen, and it was among the 23 cases with strong S14 expression. Among 10 node-positive cases with weak S14 expression, no recurrence was observed on follow-up. In contrast, of the 44 node positive cases with strong staining, 14 (32%) developed recurrent disease (p<0.0001).

Example 8

Recombinant Adenovirus

Adenovirus harboring dominant-negative and constitutively active SREBP-1c mutants are known in the art (Foretz, et al. (1999) supra). β-Galactosidase gene (negative control; Ad-β-gal) and full-length rat S14 cDNA (Kinlaw, et al. (1992) *Endocrinol.* 131:3120-3122) in both the sense orientation (Ad-S14) and antisense orientation (Ad-S14-AS) were inserted into adenoviral DNA (CLONTECH, Mountain View, Calif.) as described (Mizuguchi, et al. (1998) *Human Gene Therapy* 9:2577-2583). Viruses were propagated in HEK293 cells (ATCC, Manassas, Va.) and titered by immunocytochemical analysis of capsid protein (Rapid-Titer; CLONTECH, Mountain View, Calif.). The multiplicity of infection required for quantitative infection was determined by staining Ad-β-gal-infected wells.

Example 9

Cell Culture and Infection

T47D cells (ATCC, Manassas, Va.) were grown in RPMI 1640 plus 10 μg/mL insulin, HEK293 cells (ATCC, Manassas, Va.) in RPMI 1640, and MCF10a cells in DMEM/F12 plus 4 mg/mL insulin, 20 μg/mL epidermal growth factor, and 1 mg/mL hydrocortisone. Media contained penicillin, streptomycin, 4 mM glutamine, 25 mM glucose unless noted otherwise, and 10% fetal calf serum unless noted. Charcoal-stripped fetal calf serum (HYCLONE, Logan, Utah) was used in studies involving R5020 or R1881 (10 nM, New England Nuclear); an equal volume of ethanol vehicle was added to control cultures. Cerulenin (SIGMA, St. Louis, Mo.) was used at 10 μg/mL.

Example 10

Plasmid Transfection

T47D or HEK 293 cells were plated at 50% confluence in 75 cm² flasks and the next morning were transfected with 8 μg plasmid DNA in 48 μL FUGENE (Roche, Indianapolis, Ind.) in 5% charcoal-stripped serum-containing media without antibiotics. To ensure uniform transfection efficiency, cells were trypsinized, mixed, and redistributed into 6-well plates 8 hours later. Forty-eight hours post-transfection, culture medium was removed, and extracts prepared in reporter lysis buffer (250 μL/well; PROMEGA, Madison, Wis.). Lysates (20 μL) were assessed for luciferase activity using an LMaxII384 luminometer (MOLECULAR DEVICES, Sunnyvale, Calif.), and normalized to protein concentrations (BCA Protein Assay; Pierce, Rockland, Ill.).

Example 11

Transfection of siRNA

Cells were plated at ~70% confluency in 60-mm dishes the day before transfection with 20 μg siRNA in 333 μL diluent supplied by QIAGEN, and 120 μL of RNAIFECT Transfection Reagent (QIAGEN, Valencia, Calif.). The siRNAs (Dharmacon, Chicago, Ill.) targeted the following sequences in S14 mRNA: siRNA#1, 5'-gga aat gac ggg aca agt t-3' (SEQ ID NO:4); and siRNA#2,5'-cag ccg agg tgc aca aca t-3' (SEQ ID NO:5). Scrambled siRNAs were employed as controls. Complexes were incubated at room temperature for 15 minutes and added drop-wise to cultures. After 24 hours, cells were trypsinized and redistributed into 4 wells of a 12-well plate to ensure uniform transfection efficiency, in media containing hormone or vehicle.

Example 12

Reverse Transcriptase-PCR

Total RNA (500 ng) harvested in TRIZOL was used as template with the GIBCO/BRL "OneStep" kit. Primers (forward/reverse) for cyclophilin were 5'-gga tgg caa gca tgt ggt g-3' (SEQ ID NO:6) and 5'-tgt cca cag tca gca atg g-3' (SEQ ID NO:7); S14, 5'-cca tct gtg tgg atg tgg acc-3' (SEQ ID NO:8) and 5'-agc atc ccg gag aac tga gcc-3' (SEQ ID NO:9); SREBP-1a, 5'-tca gcg agg cgg ctt tgg agc ag-3' (SEQ ID NO:10) and 5'-cat gtc ttc gat gtc ggt cag-3' (SEQ ID NO:11; Shimomura, et al. (1997) supra); SREBP-1c, 5'-gga ggg gta ggg cca acg gcc t-3' (SEQ ID NO:12) and 5'-cat gtc ttc gaa agt gca atc c-3' (SEQ ID NO:13; Shimomura, et al. (1997) supra); and FAS, 5'-aca ggg aca acc tgg agt tct-3' (SEQ ID NO:14) and 5'-ctg tgg tcc cac ttg atg agt-3' (SEQ ID NO:15; Field, et al. (2001) *J. Lipid Res.* 42:1687-1698). S14-RP was analyzed with two sets of primers, one that amplified the entire coding region (5'-acc agg cag acc atc cc-3' (SEQ ID NO:16) and 5'-agt ttg cag tat gcc ctt ccc-3' (SEQ ID NO:17)) and a nested pair (5'-ccg ggt tag aca acg atg tt-3' (SEQ ID NO:18) and 5'-tgg ctg tac atg tac cga gag-3' (SEQ ID NO:19)). PGC-1β primers were 5'-acc tca cct cgg cac agt gct-3' (SEQ ID NO:20) and 5'-tca ccc ggc tca ttg tcc t-3' (SEQ ID NO:21), and those for CHREBP were 5'-ccg cct gag gat gcc tac gtc-3' (SEQ ID NO:22) and 5'-gga ggc ggg agt tgg taa aga-3' (SEQ ID NO:23). Sizes of the products in bp were: S14 365; SREBP-1a 80; SREBP-1c 80; FAS 159; S14-RP 724 and 132; PGC-1β 99, and CHREBP 116. Amplification was at 55° C. for 30 minutes, 94° C. for 2 minutes, followed by 15 cycles each of 94° C. for 30 seconds, 57° C. for 30 seconds, 72° C. for 1 minute; 94° C. for 30 seconds, 62° C. for 30 seconds, 72° C. for 1 minute; 94° C. for 30 seconds, 55° C. for 30 seconds, 72° C. for 1 minute, followed by extension at 72° C. for 2 minutes. Reactions using primers that did not span introns were always accompanied by a control PCR devoid of reverse transcriptase, which never yielded a product.

Example 13

Real-Time Reverse Transcriptase PCR

Total RNA was isolated using RNEASY minicolumns from cell extracts prepared with QIASHREDDER (QIAGEN, Valencia, Calif.). RNA integrity was assessed by visualization on agarose gels, and contamination with genomic DNA was excluded by failure to obtain a PCR product using primers for cyclophilin A. RNA (1 µg) was reverse-transcribed with M-MuLV reverse transcriptase and p(dt)18 (NEW ENGLAND BIOLABS, Ipswich, Mass.). Product (50 ng) was added to 96-well plates (in duplicate) with primers and SYBR Green reaction mix (PE Biosystems). PCR (BIO-RAD MYIQ ICYCLER) commenced with heat activation for AMPLITAQ GOLD DNA polymerase (Roche, Indianapolis, Ind.) (95° C. for 10 minutes), followed by denaturation (95° C. for 30 seconds), annealing (57° C. for 30 seconds), extension (72° C. for 30 seconds), and data acquisition at the end of the extension step, for 40 cycles. Dilutions of cloned cDNA fragments from each mRNA assayed were included to provide a standard curve. MYIQ Optical System Software (BIO-RAD, Waltham, Mass.) was used to assess signals during the log-linear accumulation phase, calculated as ng template per tube compared to the standard curve, which was linear across 6 logs of input. Values were normalized to the signal obtained from the same sample using primers for cyclophilin A and reported in arbitrary units. Melting curves assured that signals arose from single products, and wells without template were included to survey for contamination.

Example 14

Cell Growth

Cells (20,000/well) were seeded in 12-well plates in media containing stripped fetal calf serum. Medium was replaced after 12 hours, and 12 hours later with media containing 10 nM R1881 (or R2020) or vehicle. Media were replaced again after 3 days, and growth was assayed on the $6^{th}$ day after hormone addition. In experiments using adenovirus, cells (20,000/well) seeded in medium containing 10% fetal calf serum were infected the following morning. Media were changed after 1 hour, and again 3 days later. Cell accumulation was measured by the 3-(4,5-dimethylthiazol-2yl)-5-(3-carboxymethyphenyl)-2-(4-sulfophenyl)-2H-tetrazolium (MTS) assay (PROMEGA, Madison, Wis.). Oxidation of MTS by viable mitochondria yields a product that absorbs at 490 nM. MTS data showed a strong correlation with DNA content/well under a variety of metabolic circumstances.

Example 15

Lipid Synthesis

14-[C]-acetate (4 µCi/mL; Sigma, St. Louis, Mo.) was added to media for 3 hours, and incorporation into lipid was determined as in (Kinlaw, et al. (1995) *J. Biol. Chem.* 270: 16615-16618), using standard methods (Bligh & Dyer (1959) *Can. J. Biochem. Physiol.* 37:911-917)

Example 16

Statistical Analysis

All experiments were repeated at least once. Comparison of two groups was by two-tailed Student's t-test. Comparisons between more than two groups was by two-way analysis of variance (Wilkinson, et al. (1992) SYSTAT: Statistics, Version 5.2 Edition, p. 724, Evanston, Ill.: SYSTAT, Inc.).

Example 17

Mouse Model of Breast Cancer

To further determine the role of S14 in breast cancer, a conditional knockout model is employed. It is contemplated that a complete mammary-specific knockout will not be lethal, and that it will permit the flexibility to analyze S14 function in selected mammary epithelial subtypes or in pregnancy-dependent models using appropriate Cre-expressing mice (Wagner et al. (2003) *Mol. Cell. Biol.* 23:150-162). As such, a mice with germline transmission of a floxed S14 allele has been produced and will be used in conjunction with mice harboring transgenes for both mammary epithelial Cre recombinase expression and a mammary oncogene. In view of the nexus between Her2/neu signaling, S14, and the lipogenic breast cancer phenotype, the MMTV-Her2/neu GEM model suitable (Holland, ed. (2004) *Mammary Gland Cancer*, John Wiley).

What is claimed is:

1. A method of predicting disease-free survival of a subject with breast cancer comprising detecting the expression level of S14 consisting of SEQ ID NO: 1 in a sample obtained from a subject with breast cancer, comparing the level in the sample with a control sample, and determining whether the expression level of S14 consisting of SEQ ID NO: 1 in the sample obtained from the subject with breast cancer is comparable to the expression level of S14 consisting of SEQ ID NO: 1 in the control sample wherein a lack of overexpression of S14 consisting of SEQ ID NO: 1 in the sample compared to the control is predictive of disease-free survival.

* * * * *